(12) United States Patent
Zheng et al.

(10) Patent No.: US 10,888,462 B2
(45) Date of Patent: Jan. 12, 2021

(54) ULTRASONIC WAVE GENERATION DEVICE FOR HEARING RECOVERY TREATMENT

(71) Applicant: SHENZHEN INSTITUTES OF ADVANCED TECHNOLOGY, CHINESE ACADEMY OF SCIENCES, Shenzhen (CN)

(72) Inventors: Hairong Zheng, Shenzhen (CN); Zhengrong Lin, Shenzhen (CN); Lili Niu, Shenzhen (CN); Long Meng, Shenzhen (CN); Wei Zhou, Shenzhen (CN); Xiaowei Huang, Shenzhen (CN); Kaiyue Wang, Shenzhen (CN)

(73) Assignee: SHENZHEN INSTITUTES OF ADVANCED TECHNOLOGY, CHINESE ACADEMY OF SCIENCES, Shenzhen (CN)

( * ) Notice: Subject to any disclaimer, the term of this patent is extended or adjusted under 35 U.S.C. 154(b) by 40 days.

(21) Appl. No.: 16/474,612

(22) PCT Filed: Feb. 8, 2017

(86) PCT No.: PCT/CN2017/073107
§ 371 (c)(1),
(2) Date: Jun. 28, 2019

(87) PCT Pub. No.: WO2018/120354
PCT Pub. Date: Jul. 5, 2018

(65) Prior Publication Data
US 2019/0321229 A1    Oct. 24, 2019

(30) Foreign Application Priority Data

Dec. 28, 2016 (CN) .......................... 2016 1 1237146

(51) Int. Cl.
*H04R 25/00* (2006.01)
*A61F 11/04* (2006.01)
(Continued)

(52) U.S. Cl.
CPC ................ *A61F 11/04* (2013.01); *B06B 3/04* (2013.01); *A61N 2007/0004* (2013.01); *B06B 2201/76* (2013.01)

(58) Field of Classification Search
CPC ........ H04R 25/00; H04R 25/48; H04R 25/75; H04R 2460/13; H04R 25/353; H04R 25/606
See application file for complete search history.

(56) References Cited

U.S. PATENT DOCUMENTS 6,068,590 A    5/2000  Brisken
7,520,851 B2 * 4/2009  Davis ..................... A61B 5/121
                                                        600/25
(Continued)

FOREIGN PATENT DOCUMENTS

CN    201676079 U   12/2010
CN    104490517 A    4/2015
(Continued)

OTHER PUBLICATIONS

International Search Report & Written Opinion for PCT/CN2017/073107, pp. 1-8 (English translation included, dated Sep. 27, 2017, pp. 1-3).

Primary Examiner — Amir H Etesam

(57) ABSTRACT

Disclosed is an ultrasonic wave generation device for hearing recovery treatment, including an ultrasonic wave generation part. The ultrasonic wave generation part comprises a reference time-delay determination module, an emission sequence parameter determination module and an ultrasonic transducer module. The ultrasonic transducer module is used for emitting actual ultrasonic waves, and the efficiency and (Continued)

precision are improved by focusing by means of a plurality of array elements.

10 Claims, 3 Drawing Sheets

(51) Int. Cl.
*B06B 3/04* (2006.01)
*A61N 7/00* (2006.01)

(56) References Cited

U.S. PATENT DOCUMENTS

2007/0282397 A1* 12/2007 Ball .................. A61N 1/36038
607/57
2012/0245406 A1 9/2012 Aghamohammadi
2017/0291044 A1 10/2017 Zheng et al.

FOREIGN PATENT DOCUMENTS

| | | |
|---|---|---|
| CN | 104548390 A | 4/2015 |
| WO | 2007119505 A1 | 10/2007 |
| WO | 2015142764 A1 | 9/2015 |

\* cited by examiner

ULTRASONIC WAVE GENERATION DEVICE FOR HEARING RECOVERY TREATMENT

CROSS-REFERENCE TO RELATED APPLICATIONS

This application is the National Stage of International Application No. PCT/CN2017/073107, filed Feb. 8, 2017, which claims priority to Chinese Application No. CN 201611237146.3, filed Dec. 28, 2016, which are entirely incorporated herein by reference.

TECHNICAL FIELD

The present disclosure relates to the field of application of ultrasonic waves, and particularly to an ultrasonic wave generation device for hearing recovery treatment.

BACKGROUND ART

Sensorineural hearing loss is a common and frequently-occurring disease in the world. At present, there are at least 20.57 million people suffering from hearing loss in China, about 800,000 of them are children, and the number of people increases at a rate of 80,000 per year. Among the people suffering from hearing loss, sensorineural hearing loss is clinically the commonest. At present, there are plenty of clinical therapeutic means (drug treatment, treatment with traditional Chinese medicine, wearing a hearing aid, artificial cochlea implantation (cochlear implantation), etc.), but they are substantially palliative intervention means based on different degrees of hearing loss. Real-time intervention and treatment of progressive functional loss (called auditory deprivation, or progressive decline of auditory central nervous function) of the auditory pathway nuclei based on hearing loss remain impotent.

The studies show that the lesion of most of the people suffering from complete hearing loss is mainly located in the auditory sensor part of the inner ear, and auditory nerves are usually intact. The methods for clinically treating sensorineural hearing loss mainly include: drug treatment, treatment with traditional Chinese medicine, wearing a hearing aid, and artificial cochlea implantation.

These treatment methods each have advantages and disadvantages, and on the whole, these treatment methods most have the problems of long treatment period, great side effects, etc.

SUMMARY

An object of the present disclosure is to provide an ultrasonic wave generation device for hearing recovery treatment, so as to improve the convenience in real-time intervention and treatment of hearing loss.

In a first aspect, an embodiment of the present disclosure provides a device, e.g., an ultrasonic wave generation device for hearing recovery treatment, comprising: a wearing part and an ultrasonic wave generation part provided on the wearing part;

the ultrasonic wave generation part comprises: a reference time-delay determination module, an emission sequence parameter determination module (an module for determining emission sequence parameters) and an ultrasonic transducer module, the ultrasonic transducer module comprising an activation control unit provided on the wearing part and a plurality of array elements arranged in an array; wherein each array element is electrically connected with the activation control unit through an independent line respectively;

the reference time-delay determination module is configured to calculate a reference time delay of each array element when emitting an excitation pulse signal;

the emission sequence parameter determination module is configured to determine an emission sequence parameter of each array element; and the activation control unit is configured to control, according to the reference time delay and the emission sequence parameter of each array element, each array element to generate an excitation pulse signal, so that the excitation pulse signal emitted by each array element is focused on a target area.

In connection with the first aspect, an embodiment of the present disclosure provides a first possible implementation mode of the first aspect, in which the reference time-delay determination module comprises:

an acoustic parameter acquisition unit configured to acquire acoustic parameters of the target area, wherein the acoustic parameters include density, sound velocity and attenuation coefficient; and a calculation unit configured to calculate a reference time delay of each array element according to the acoustic parameters, the relative position information of the target area and the relative position information of the array element, which are acquired in advance.

In connection with the first aspect, an embodiment of the present disclosure provides a second possible implementation mode of the first aspect, in which the acoustic parameter acquisition unit is further configured to establish a three-dimensional model of cochlea according to a scan image, and calculate the acoustic parameters according to the three-dimensional cochlea model and relative position information between the array elements and the target area.

In connection with the first aspect, an embodiment of the present disclosure provides a third possible implementation mode of the first aspect, in which the wearing part is in the shape of a flat plate and comprises a clamping part and a fixing part provided at the rear of the clamping part, and each array element is located on one side surface of the fixing part.

In connection with the first aspect, an embodiment of the present disclosure provides a fourth possible implementation mode of the first aspect, in which the emission sequence parameter determination module is further configured to calculate an emission sequence parameter of each array element according to the position of a cochlear lesion, the size of the cochlea and the severity of the cochlear lesion that are acquired in advance.

In connection with the first aspect, an embodiment of the present disclosure provides a fifth possible implementation mode of the first aspect, in which a plurality of ultrasonic transducer modules are provided, and the ultrasonic wave generation part further comprises: an ultrasonic transducer determination module configured to determine, according to the location and the size of the lesion tissue and the severity of the lesion, a corresponding ultrasonic transducer module to be used.

In connection with the first aspect, an embodiment of the present disclosure provides a sixth possible implementation mode of the first aspect, in which the target area is the cochlea.

In connection with the first aspect, an embodiment of the present disclosure provides a seventh possible implementation mode of the first aspect, in which the clamping part has a crescent-like shape and is adapted to the outer contour of an ear.

In connection with the first aspect, an embodiment of the present disclosure provides an eighth possible implementation mode of the first aspect, in which an elastic contact layer is provided on an inner surface of the clamping part.

In connection with the first aspect, an embodiment of the present disclosure provides a ninth possible implementation mode of the first aspect, in which the wearing part comprises a protective housing in shape of a flat plate and an adhesive layer, the plurality of array elements are all located inside the protective housing, and the adhesive layer is located on one side surface of the protective housing.

Compared with the prior art in which the treatment of hearing loss requires high treatment cost and causes inconvenience to the user (for example, wearing a hearing aid for a long time), and the treatment effect differs greatly from person to person, the device, e.g., the ultrasonic wave generation device for hearing recovery treatment, provided by the embodiment of the present disclosure is provided with an ultrasonic wave generation part in which a reference time-delay determination module and an emission sequence parameter determination module are configured to adjust the parameters and an ultrasonic transducer is configured to emit actual ultrasonic waves, and the efficiency and precision are improved by focusing with a plurality of array elements; moreover, the device is further provided with a wearing part, so that a user can directly wear the device on the ears by using the wearing part, which improves the convenience of use and the effect of real-time intervention and treatment.

In order to make the above objects, features and advantages of the present disclosure more apparent and easily understandable, detailed description is made below in connection with preferred embodiments with reference to the accompanying drawings.

BRIEF DESCRIPTION OF DRAWINGS

In order to more clearly illustrate the technical solutions of the embodiments of the present disclosure, brief description is made below on the drawings required to be used in the embodiments. It should be understood that the following drawings only illustrate some of the embodiments of the present disclosure and thus shall not be regarded as a limitation on the scope, and for a person of ordinary skills in the art, other related drawings may be obtained from these drawings without inventive effort.

DETAILED DESCRIPTION OF EMBODIMENTS

Figure 1:
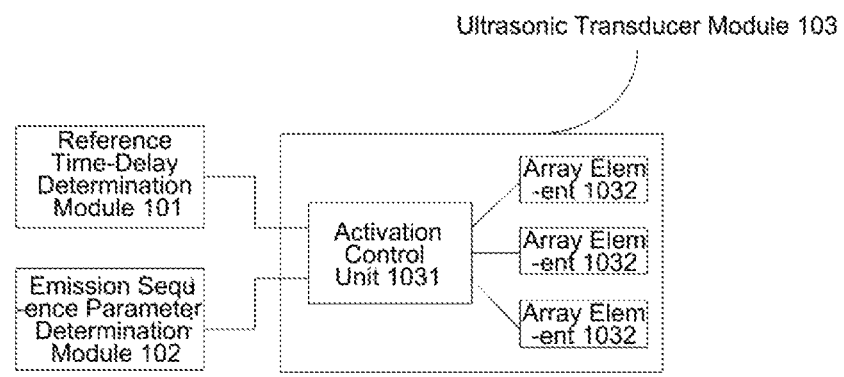
FIG. 1 is a structural diagram of basic modules of a device, e.g., an ultrasonic wave generation device for hearing recovery treatment, provided in an embodiment of the present disclosure.

The technical solutions in the embodiments of the present disclosure will be clearly and completely described below with reference to the drawings of the embodiments of the present disclosure. It is apparent that the embodiments described are only some of the embodiments of the present disclosure, rather than all of the embodiments of the present disclosure. Generally, the components of the embodiments of the present disclosure described and illustrated in the drawings herein may be arranged and designed in various different configurations. Thus, the following detailed description of the embodiments of the present disclosure provided in the drawings is not intended to limit the scope of the present disclosure claimed, but only represents the selected embodiments of the present disclosure. All the other embodiments that are obtained by a person skilled in the art on the basis of the embodiments of the present disclosure without inventive effort shall be covered by the protection scope of the present disclosure.

For such a disease as hearing loss, there have been a variety of targeted treatment solutions in the related art, which are specifically, for example, drug treatment, treatment with traditional Chinese medicine, wearing a hearing aid, and artificial cochlea implantation. These solutions are described separately below.

Drug treatment: Clinically, the main means for preventing and treating sensorineural hearing loss is still the use of drugs. The drugs commonly used for the prevention and treatment of sensorineural hearing loss mainly include: cochlear injection of corticosteroid hormone, antioxidants, mitochondrial enhancers, glutamate antagonists, nitric oxide synthetase inhibitors, vasodilators, neurotrophic factors, gene therapy and stem cell therapy. Glucocorticoids can be used to treat sudden sensorineural hearing loss (SSHL) resulting from various causes (e.g., idiopathic, viral, vascular, trauma, and other causes). Glucocorticoids play multiple roles, e.g., immunosuppression, anti-infection, membrane stabilization, regulation of sodium transport, signal transduction, etc. (Al-Mana D, Ceranic B, Djahanbakhch O, et al. Hormones and the auditory system: a review of physiology and pathophysiology. Neuroscience, 2008, 153(4): 881-900.). The basic role of antioxidants is to eliminate ROS, and reduce the toxic effect of free radicals, and they are often used in combination with mitochondrial enhancers for the treatment of sensorineural hearing loss (Korver K D, Rybak L P, Whitworth C, et al. Round window application of D-methionine provides complete cisplatin otoprotection. Otolaryngol Head Neck Surg, 2002, 126 (6): 683-689.). The use of glutamate antagonists can protect against hearing loss caused by noise and ototoxicity (DIAO Mingfang, ZHANG Yanmin, LIU Haiying, et al. Study of Protective Effect of MK2801 on Noise-induced Hearing Impairment 3. Journal of Clinical Otorhinolaryngology Head and Neck Surgery, 2005, 19 (1): 27-30.). The use of nitric oxide synthetase inhibitors, vasodilators and neurotrophic factors mainly serves to provide nutritional protection for damaged cochlea. Gene therapy and stem cell therapy are promising for the rehabilitation of the people suffering from hearing loss. Gene therapy is to introduce genes into the target cells of a human body in a certain way to correct genetic defects or play a therapeutic role so as to achieve the object of treating diseases. Stem cell therapy is to separate stem cells and make them differentiate in a specific direction, so that healthy tissue cells can be used to replace damaged tissue cells in the patient's body, thereby achieving the object of treating diseases. At present, these two methods are in the stage of research and experiment, and great progress has been made, meanwhile there also exist many problems.

Treatment with traditional Chinese medicine: In recent years, there have been lots of clinical reports about treatment of sensorineural hearing loss with traditional Chinese medicine, and common treatments are: therapy principally by traditional Chinese medicine, acupuncture, and combination therapy of acupuncture and traditional Chinese medicine. In China, treatment of sensorineural hearing loss with traditional Chinese medicine is also relatively common, e.g., CONGER mixture (i.e. a mixture for improving hearing), SHUXUETONG (i.e. an agent for activating blood circulation and dredging channels and activating collaterals), GUSHENSHUER tablet (i.e. a tablet for treating sensorineural deafness and tinnitus), etc. ZHONG Qu et al. randomly divided 60 people suffering from sensorineural hearing loss into groups, treated them with Conger mixture and conventional Western medicine, separately, and the results showed that the total effective rate was 82.36% in the group treated with traditional Chinese medicine and the total effective rate was 59.38% in the group treated with conventional Western medicine, significant differences existing therebetween (ZHONG Qu, ZHENG Taoxiao, FENG Zhirong, ZOU Wenrong, YANG Chunying. Randomized Controlled Study on Conger-Mixture for Treatment of Sensorineural Hearing loss [J]. Chinese Archives of Traditional Chinese Medicine, 2011, 29 (8): 1752-1753). Acupuncture is widely used in the treatment of sensorineural hearing loss. ZHU Zhiqiang et al. treated 75 cases of sensorineural hearing loss by needling, with the total effective rate of 85.35% (ZHU Zhiqiang, LU Ming. Treatment of 75 Cases of Sensorineural Hearing Loss and Tinnitus by Needling [J]. Shanghai Journal of Acupuncture and Moxibustion. 2009; 28 (2): 102). Combination therapy of acupuncture and traditional Chinese medicine: WANG Suqiang randomly divided 60 people suffering from sudden hearing loss into groups, treated the treatment group with balanced acupuncture combined with oral administration of traditional Chinese medicine, and treated the control group with conventional therapy of Western medicine such as hormone; and the results showed that the total effective rate was 93.3% in the treatment group and the total effective rate was 66.7% in the control group, and the comparison between the two groups is of statistical significance (WANG Suqiang. Treatment of 30 Cases of Sudden Hearing Loss by Balanced Acupuncture Combined with Traditional Chinese Medicine [J]. Journal of Clinical Acupuncture and Moxibustion, 2011, 27 (1): 40-41). It can be seen from the above that traditional Chinese medicine has been widely used in clinical treatment of sensorineural hearing loss, with a high effective rate.

Wearing a hearing aid: A hearing aid is a small loudspeaker that amplifies sounds that cannot be heard originally, and further makes use of the residual hearing of the people with hearing impairment, so that the sounds can be sent to the auditory center of the brain to be felt. A hearing aid is essentially composed of five parts, i.e., a microphone, an amplifier, an earphone, a power supply and a volume control. Hearing aids are classified into air conduction hearing aids and bone conduction hearing aids according to the manner of conduction; and are classified into pocket hearing aids, eyeglass hearing aids, hairpin hearing aids, behind-the-ear hearing aids, in-the-ear hearing aids, in-ear canal hearing aids, and completely-in-ear canal hearing aids according to the way of use. Wearing hearing aids helps to improve the abilities of sound source locating, noise reduction and speech comprehension, enhance the effect of binaural loudness integration, avoid delayed auditory deprivation effect and delay the decline of auditory nerve function, and therefore helps to prevent the progressive decline of auditory central nervous function of sensorineural hearing loss.

Artificial cochlea implantation: An artificial cochlea is an electronic device which recovers or reconstructs the auditory function of the people suffering from hearing loss by converting sounds into electrical signals with certain encoded form by means of an external speech processor and directly exciting the auditory nerve by means of an electrode system implanted in the body. In recent years, with the development of electronic technology, computer technology, phonetics, electrophysiology, materials science and otomicrosurgery, artificial cochleae have been put into clinical application from experimental research. Artificial cochleae are now used around the world as a routine treatment for severe to total hearing loss. Electrical cochleae can enable the patients to regain hearing by using electrodes implanted in the inner ear to bypass the damaged part of the inner ear and direct stimulate the auditory nerve with electrical current, which cannot be achieved by hearing aids. At present, the multichannel electronic cochlear implant surgery in China has not been fully popularized, and more than 1,400 cases in total have been carried out in China since 1996, but with the development of technology, it has benefited the vast number of people suffering from sensorineural hearing loss.

However, each of the above treatment methods has its own disadvantages. For example:

Drug treatment: Drug treatment is still a conventional method for treating sensorineural hearing loss at present. There are many kinds of drugs for sensorineural hearing loss, but they are substantially based on a certain pharmacological effect of the drug, and cannot completely avoid other adverse effects to achieve single therapeutic effect. Moreover, different administration methods lead to different pharmaceutical effects, for example, oral administration is convenient, but with relatively low drug concentration and ordinary therapeutic effect; and the administration of cochlear injection can solve the problem of drug concentration well, but results in poor compliance with the patients, and makes the body vulnerable to invasive impacts.

Treatment with traditional Chinese medicine: in China, although there are many clinical applications and reports on the treatment of sensorineural hearing loss with traditional Chinese medicine, the quality of the literatures is usually relatively low, most of them are small sample clinical observations, and randomized control is not truly achieved in many studies, thus they cannot be a powerful proof of the effectiveness of treatment with traditional Chinese medicine. In terms of therapeutic effect, traditional Chinese medicine mainly serves for prevention and protection, and takes effect relatively slowly, and the study on the mechanism thereof is not very clear. Meanwhile, some people hold that the treatment of sensorineural hearing loss with acupuncture is still in the initial stage, its treatment efficacy needs to be further demonstrated by high-quality experiments. Thus, the effectiveness of traditional Chinese medicine in the treatment of sensorineural hearing loss is still controversial.

Wearing a hearing aid: For people suffering from hearing loss, they have commonness, but also differ greatly from one another. Among them, there are congenital hearing loss and acquired hearing loss, hereditary and non-hereditary hearing loss, traumatic hearing loss and ototoxic hearing loss, and senile hearing loss and hearing loss caused by various pathological changes. These hearing losses result from different causes, have different degrees, and also have different frequency bands of hearing loss, which therefore imposes special requirements on the adaptation of hearing aids. Limited by power, hearing aids can only be adapted to some people suffering from mild hearing loss. The frequency response of hearing aids must comply with the requirements of the audiogram, i.e., the frequencies that need to be compensated must meet the requirements of decibel (dB) of hearing loss, while the frequencies in non-emphasized compensation area must be attenuated to meet the requirement, otherwise, there will be either insufficient compensation at the emphasized frequency bands that need to be compensated, or insufficient attenuation in the frequency bands that need to be attenuated, and as a result, small sounds cannot be heard (emphasized compensation area), and large sounds cause "ear vibration" (non-emphasized compensation area). If the user is biased towards neural hearing loss, the air-conduction hearing aid can hardly cause vibration of the ossicular chain, and can hardly achieve hearing effect with the inner ear, and has slight effect on severe hearing loss. In the case where the compensation curve is not appropriate, the greater the sound of the earphone is, the more likely it is to cause fainting or vomiting.

Artificial cochlea implantation: Although artificial cochleae can have better effects in the treatment of sensorineural hearing loss, due to the limitations of the factors, such as price and surgery, at present, the multi-channel electronic cochlear implant surgery in China has not been fully popularized. Moreover, due to the relatively high requirements of this surgery, in China, only a few Grade III Level A hospitals, e.g., Tongren Hospital, the Chinese PLA General Hospital, Peking Union Medical College Hospital in Beijing, Eye & ENT Hospital of Fudan University in Shanghai, etc. are able to perform the electronic cochlear implant surgery. Furthermore, in general, only three countries, i.e., Australia, the United states and Austria, around the world can produce artificial cochleae at present. The cost of each of the artificial cochleae used in domestic hospitals varies from more than one hundred thousand yuan to more than two hundred thousand yuan, plus the treatment cost, the total cost of surgery is generally about 200,000 yuan. Moreover, not all hearing losses can be recovered by cochlear implant surgery. The purpose of recovering hearing by cochlear implant surgery can only be achieved for sensorineural hearing loss, but not for neural hearing loss. Just for this reason, before a decision is made as to whether or not the surgery is performed, an auditory assessment is always made on the patient by an audiologist in order to determine the nature and the degree of hearing loss of the patient. It is generally believed that only the patients who are unable to perceive sounds with a volume greater than 90 decibels are suitable for treatment of electronic cochlear implant surgery. In other words, the volume of 90 decibels is a criterion for determining whether a patient can be treated by cochlear implant surgery. For the patients after the surgery, the recovery effect also varies from person to person, and it generally takes three to five years for them to recover.

It can be seen that each of the above-mentioned treatment methods has its own disadvantages. In view of this, the inventor of the present disclosure believes that better therapeutic effect can be achieved by using ultrasonic therapy, and therefore has developed an ultrasonic wave generation device for hearing recovery treatment, which, as shown in FIGS. 1 to 6, comprises: a wearing part 301 and an ultrasonic wave generation part provided on the wearing part 301;

wherein the ultrasonic wave generation part comprises: a reference time-delay determination module 101, an emission sequence parameter determination module 102 and an ultrasonic transducer module 103, wherein the ultrasonic transducer module 103 comprises an activation control unit 1031 provided on the wearing part 301 and a plurality of array elements 1032 arranged in array; each array element 1032 is electrically connected with the activation control unit 1031 through an independent line respectively;

the reference time-delay determination module 101 is configured to calculate a reference time delay of each array element 1032 when emitting an excitation pulse signal;

the emission sequence parameter determination module 102 is configured to determine an emission sequence parameter of each array element 1032; and the activation control unit 1031 is configured to control, according to the reference time delay and the emission sequence parameter of each array element 1032, each array element 1032 to generate the excitation pulse signal, so that the excitation pulse signal emitted by each array element 1032 is focused on a target area.

The ultrasonic wave generation device for hearing recovery treatment described above mainly has two parts, one is the part for emitting ultrasonic waves, i.e., the ultrasonic wave generation part, which serves to generate ultrasonic waves for treating hearing loss; and the other is the part to be carried by the patient, i.e., the wearing part 301, which serves to carry the ultrasonic wave generation part in the vicinity of an ear of the patient.

Figure 2:
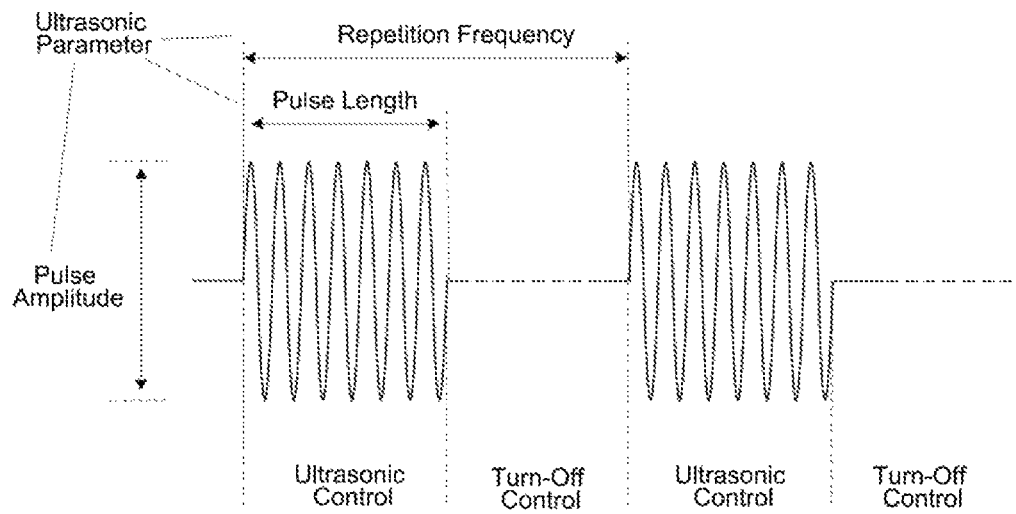
FIG. 2 is a waveform diagram of an excitation pulse signal emitted by an array element of the device, e.g., the ultrasonic wave generation device for hearing recovery treatment, provided in an embodiment of the present disclosure.
Figure 3:
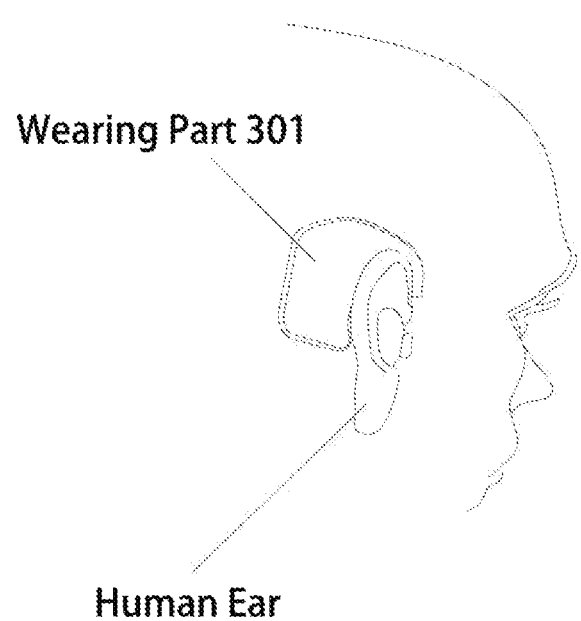
FIG. 3 is a schematic diagram showing wearing of the device, e.g., the ultrasonic wave generation device for hearing recovery treatment, provided in an embodiment of the present disclosure on a human ear.
Figure 4:
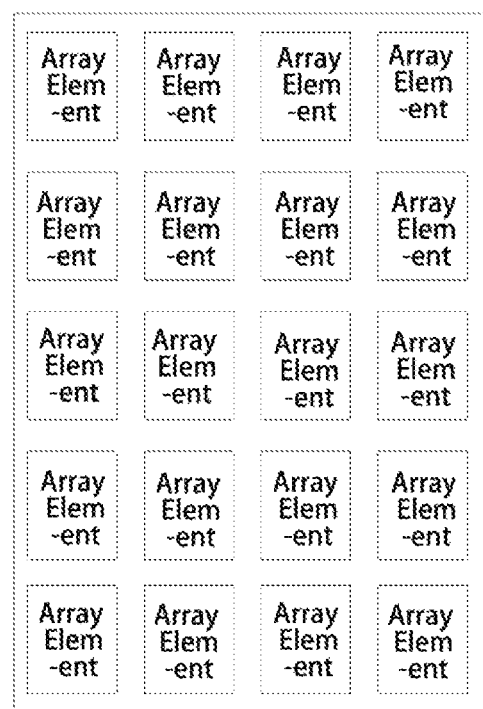
FIG. 4 is a schematic diagram showing an arrangement of a plurality of array elements of the device, e.g., the ultrasonic wave generation device for hearing recovery treatment, provided in an embodiment of the present disclosure.
Figure 5:
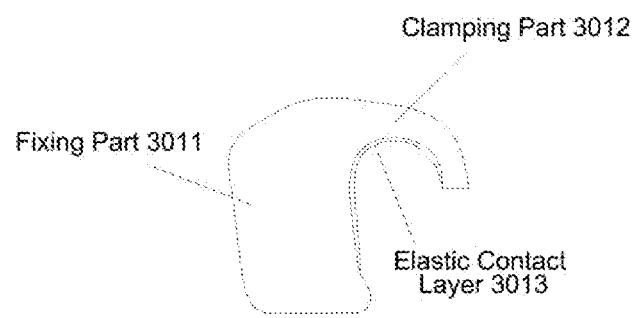
FIG. 5 is a schematic diagram of a wearing part of the device, e.g., the ultrasonic wave generation device for hearing recovery treatment, provided in an embodiment of the present disclosure.

Specifically, the reference time-delay determination module 101 and the emission sequence parameter determination module 102 are each electrically connected with the activation control unit 1031 respectively. The function of the reference time-delay determination module 101 is to adjust the position of focusing, and the principle thereof is achieving adjustment in depth by adjusting the phase delays of emitted signals from different array elements 1032, and thereby ensuring the accuracy of the ultrasonic therapy. The position of focusing is the cochlea. The function of the emission sequence parameter determination module 102 is to determine the main parameters (i.e., parameters other than reference delays) of emitted signal from each array element 1032. Since the patients differ from each other in condition and physique (the parameters such as the thickness of skin and skull), it is preferable to set emission sequence parameters corresponding to the patient to ensure the accuracy and efficiency of focusing ultrasonic waves. In the above, the emission sequence parameters include: pulse frequency, pulse duration, pulse length, pulse repetition frequency and pulse strength, and these emission sequence parameters above described can be adjusted simultaneously by the emission sequence parameter determination module 102, or only one or several of them may be adjusted, or reserved emission sequence parameters may be used. As shown in FIG. 2, the embodiment of these several parameters in one waveform is shown.

Specifically, the reference time-delay determination module comprises:

an acoustic parameter acquisition unit configured to acquire acoustic parameters of the target area, wherein the acoustic parameters include density, sound velocity and attenuation coefficient; and a calculation unit configured to calculate a reference time delay of each array element according to relative position information of the target area, relative position information of the array element and the acoustic parameters which are acquired in advance.

The acoustic parameter acquisition unit is further configured to establish a three-dimensional cochlea model according to a scan image, and calculate the acoustic parameters according to the three-dimensional cochlea model and relative position information between each array element and the target area (mainly the human body tissues that the ultrasonic waves emitted by the array elements pass through during their travel to the target area).

More specifically, the function of the reference time-delay determination module is to ensure that the ultrasonic waves emitted by each array element are all in a peak state or in a trough state, when reaching the target area.

Next, the specific working flow of the reference time-delay determination module is described as follows:

(1) A three-dimensional magnetic resonance imaging scan and a three-dimensional CT imaging scan are performed on an animal head or a human head first to obtain a scan image (the scan image including specific parameters), and then a three-dimensional cochlea model is established, and is introduced into a main control computer to complete cochlea locating.

(2) The structure information of human tissues in the vicinity of the target area, e.g., the information such as the structural shape and size of the skull and tissues around the cochlea, is obtained according to the above-mentioned three-dimensional cochlea model, and after the human tissue structures between the array elements and the target area are determined, acoustic parameters (such as various acoustic parameters of the skull and tissues, the acoustic parameters here including, but not limited to, density, sound velocity, attenuation coefficient, etc.) of the human tissue structures in the vicinity of the target area are calculated using empirical formulas or other methods. A three-dimensional digital model of an ultrasonic transducer array is established according to the structural shape of the ultrasonic transducer array (mainly the relative position information of the array elements and the relative position of the three-dimensional cochlea model) and the acoustic parameters (mainly the size of the human tissue structures in the vicinity of the target area), so as to obtain the reference time delay of each array element (it should be noted that each array element has a different reference time delay, and therefore, the reference time delay of each array element needs to be calculated separately according to the relative positional relation between each array element and the cochlea). In the specific implementation, it is feasible to input these acoustic parameters, together with the three-dimensional digital model of the ultrasonic transducer array, into a simulation software for ultrasonic time reversal, and adjust to position the virtual space positions of the above two three-dimensional digital models according to the desired actual space positions to be used (that is, adjusting the same according to the actual relative position between the array elements and the target area after the ultrasonic wave generation device is worn by the patient). The reference time delays are then calculated by means of the simulation software for ultrasonic time reversal, that is, the reference time delays are calculated according to the propagation distance and the corresponding acoustic parameters.

(3) The function of the simulation software for ultrasonic time reversal is to place a virtual sound source(s) at one or more positions where focusing is needed, and simulate the propagation state of ultrasonic waves emitted by the sound source(s) in the three-dimensional digital model of head, and when the ultrasonic waves propagate to the virtual space position where the ultrasonic transducer array is located, the software can simulate the sound intensity signal and the sound pressure signal of the ultrasonic waves on the surface of the ultrasonic transducer array, and further simulate a voltage signal of the ultrasonic transducers obtained after piezoelectric conversion. The voltage signal is subjected to time reversal (inversion in time sequence) to obtain an accurate voltage signal, and then the accurate voltage signal is used to excite the ultrasonic transducer array, the generated ultrasonic waves will be focused at the one or more positions where the virtual sound source(s) is(are) placed in the previous step. Therefore, by means of the software, it is possible to obtain the ultrasonic emission sequences and the reference time delays that are required for stimulating the cochlea and capable of achieving transcranial focusing. In addition, the time reversal method will still lead to the formation of sound field distribution with a certain intensity in undesired focusing areas, and for these areas where no stimulation is desired, the above-mentioned method may be used to place a virtual sound source first to obtain a time reversal signal, and then emit a time reversal ultrasonic signal of a negative phase to eliminate the intensity of the sound field in the respective area, which can further improve the accuracy, effectiveness and safety of targeted neural regulation.

(4) The animal or human head that needs to be subjected to cochlear ultrasonic stimulation is fixed, by a head fixing and positioning device, at a designated position in a magnetic resonance imaging system, and the ultrasonic transducer array is also fixed according to a predetermined position. The main control computer gives instructions, and an ultrasonic emitting/receiving control system is employed to control the ultrasonic transducer array (mainly meant to control the array elements) to emit ultrasonic waves according to an ultrasonic emission sequence for transcranial focusing. By using a special imaging sequence of the magnetic resonance imaging system, the shape and position of the focal point of the sound field after the ultrasonic waves have passed through the skull are observed. According to the actual measurement, combined with the three-dimensional digital model of the head, the ultrasonic emission sequence is further adjusted to improve the shape and position of the focal point of ultrasonic transcranial focusing so as to meet the requirements of ultrasonic cochlear stimulation.

(5) Ultrasonic deep brain stimulation is performed on the cochlea planned to be stimulated, and the effects of the stimulation are observed and evaluated by the technology such as functional magnetic resonance imaging. Further fine adjustment (e.g., adjustment of the reference time delays and emission sequence parameters) to the ultrasonic focusing position may also be performed as desired.

At present, since the effect of ultrasonic focusing is tested according to the above three-dimensional positioning model of cochlea, the selected emission sequence parameters are substantially the same for each array element. Different neural regulation functions are realized by adjusting different ultrasonic emission sequence parameters (frequency, PRF (Pulse Repetition Frequency), intensity, pulse duration, etc.). At present, since the frequency is substantially the same for each single array element, the current experiments are mainly testing the excitatory activation effect on the cochlea based on different PRF values (activation effect occurs when PRF is equal to or greater than 500 Hz).

Each array element 1032 is electrically connected with the activation control unit 1031 through an independent line respectively, which ensures that each array element 1032 can operate independently and different array elements 1032 will not affect each other.

In the solution provided by the present disclosure, the array elements 1032 are arranged in an array, which mainly serves to facilitate unified calculation. The array elements 1032 are at different positions relative to the cochlea, and this makes it necessary to set different emission sequence parameters for different array elements 1032, and at the same time, if the array elements 1032 are positioned disorderly, the difficulty of calculation becomes higher, which is not conducive to practical use. Preferably, 20 array elements 1032 in total are provided, which are arranged in 4 columns and 5 rows.

Specifically, the wearing part 301 is in shape of a flat plate and the wearing part 301 comprises a clamping part 3012 and a fixing part 3011 provided at the rear of the clamping part 3012, and each array element 1032 is located on one side surface of the fixing part 3011. The clamping part 3012 serves the function of fixing the wearing part 301 to the ear of the patient. Preferably, the clamping part 3012 has a crescent-like shape and is adapted to the outer contour of an ear so as to be easily worn on the ear. Furthermore, an elastic contact layer 3013 is provided on an inner surface of the clamping part 3012 in order to alleviate the patient's discomfort caused by tight clamping at the time of wearing. An adhesive layer may also be provided on one side of the clamping part (the side close to the skin of the patient) in order to improve the stability of the fixing.

In addition to the above-described method of fixing the ultrasonic wave generation device for hearing recovery treatment to the body of a patient by using a clamping part, the present disclosure further provides a method of fixing the ultrasonic wave generation device for hearing recovery treatment to the body of a patient by providing an adhesive layer. Specifically, the wearing part comprises a protective housing in shape of flat plate and an adhesive layer, the plurality of array elements are all located inside the protective housing, and the adhesive layer is located on one side surface of the protective housing. When in use, the adhesive layer may be adhered to a position between the head and a human ear by the patient, so as to achieve the effect of fixing.

Further, in the device provided in the present disclosure, the emission sequence parameter determination module 102 is further configured to calculate an emission sequence parameter of each array element 1032 according to the position of a cochlear lesion, the size of the cochlea and the severity of the cochlear lesion that are acquired in advance. That is, the several parameters, i.e., the position of a cochlear lesion, the size of the cochlea and the severity of the cochlear lesion, are taken into account at the time of calculating the emission sequence parameters.

Preferably, the plurality of array elements 1032 are arranged in a square array.

Due to the difference among the physique of the patients, a plurality of ultrasonic transducer modules 103 may be provided, and different ultrasonic transducer modules 103 have certain differences in efficacy. Therefore, in the device provided in the present disclosure, a plurality of ultrasonic transducer modules 103 are provided, and the ultrasonic wave generation part further comprises: an ultrasonic transducer determination module configured to determine the use of corresponding ultrasonic transducer modules 103 according to the position and the size of the lesion tissue and the severity of the lesion.

Figure 6:
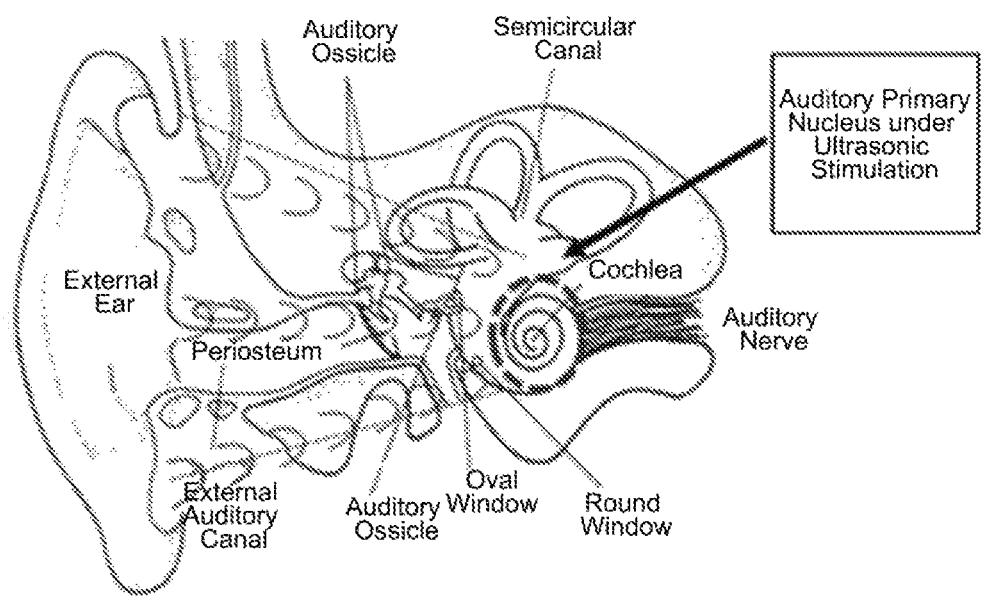
FIG. 6 is a schematic diagram of propagation of ultrasonic wave of the device, e.g., the ultrasonic wave generation device for hearing recovery treatment, provided in an embodiment of the present disclosure when in operation.

Seeing the technical solution provided by the present disclosure as a whole, the present disclosure proposes a new technique of real-time intervention and treatment of sensorineural hearing loss by ultrasonic waves, based on the fact that ultrasonic wave, which is a novel, non-invasive and safe neural regulation mode, can stimulate the auditory primary conduction pathway in an accurate and real-time manner so as to improve the progressive decline of auditory central nervous function caused by hearing loss. Ultrasonic intervention in the cochlea of the people suffering from sensorineural hearing loss is achieved by the ultrasonic plane transducer with multiple array elements 1032 is deeply focused on the cochlea. The stimulation device is light and easily portable, and can realize the effect of real-time ultrasonic intervention. The entire device comprises two parts, i.e., the ultrasonic wave generation part and the wearing part 301, and the two parts cooperate with each other to achieve better effects. In FIG. 6, the dashed circle represents the auditory cochlear nucleus under the effect of ultrasonic focusing, and the plurality of semicircular curves arranged in a stacked manner represent the propagation paths of ultrasonic waves at different sites.

In one embodiment, each array element 1032 is a piezoelectric element, such as a piezoelectric ceramic element. As an example, the principle of generation of ultrasonic waves of each array element 1032 (piezoelectric ceramic element) is: the frequency of voltage change-the frequency of piezoelectric ceramic-the frequency of ultrasonic waves. Each piezoelectric ceramic has a natural frequency (related to the shape, length, width, height and material thereof), and generally, a voltage consistent with the natural frequency is used to excite ultrasonic waves, and resonance occurs when the frequencies are the consistent with each other, radiating the maximum ultrasonic energy. The force of ultrasonic radiation acts on the lesion area of the cochlea, which provides new prevention and treatment means for sensorineural hearing loss. Moreover, with the design of the device provided in the present disclosure, the whole device is smaller and can be used more flexibly, and the accuracy of focusing can be improved.

When in use, each array element 1032 is different in the geometrical distance from the lesion area (cochlea), and in order to ensure that the energy of ultrasonic waves emitted by each array element 1032 on the ultrasonic transducer reaches a single position (cochlea) in phase (with a same phase), it is further required to adjust the phase of the excitation signal by the reference time-delay determination module 101 (the array elements 1032 do not have the same emission time, then the in-phase superposition of the ultrasonic waves is enhanced at the focal point, while the out-of-phase superposition is weakened at other positions). Thus, a ultrasonic transducer selection means comprises the reference time-delay determination module 101, which serves the function of delaying the excitation pulse signals of each excitation channel of the selected ultrasonic transducer, so as to control phase delay of the signal emission of each array element 1032 and achieve the adjustment of focusing depth of the ultrasonic transducer.

The present disclosure further relates to the above device's use for cochlear nerve stimulation. The present disclosure further relates to the above device's use for hearing recovery. The present disclosure further relates to the above device's use for the treatment and/or prevention of sensorineural hearing loss.

The present disclosure further relates to a method of improving, preventing or/treating progressive decline in auditory central nervous function or hearing deprivation disease by stimulating in real time the auditory primary conduction pathway with ultrasonic waves. In one embodiment, the progressive decline in auditory central nervous function is caused by hearing loss.

The present disclosure further relates to a method of preventing and/or treating sensorineural hearing loss, comprising: stimulating auditory primary conduction pathway, cochlea or a combination thereof with ultrasonic waves. In one embodiment, ultrasonic waves are focused on the cochlea. In one embodiment, ultrasonic waves are applied to the auditory primary conduction pathway and the cochlear nucleus. In one embodiment, ultrasonic waves are applied to the lesion area of the cochlea. The present disclosure further relates to a method of preventing and/or treating sensorineural hearing loss, the method being implemented by a device comprising an ultrasonic transducer module having a plurality of array elements, and comprising:

calculating a reference time delay of each array element when emitting an excitation pulse signal;

determining an emission sequence parameter of each array element; and controlling, according to the reference time delay and the emission sequence parameter of each array element, each array element to generate an excitation pulse signal, so that the excitation pulse signal emitted by each array element is focused on a target area.

In one embodiment, the ultrasonic transducer module is selected according to the object of intervention and the position of the cochlea, such that the sound waves emitted by the selected ultrasonic transducer module are suitable for penetrating the skin and the skull so as to act on a particular lesion area.

In one embodiment, the method further comprises: evaluating sensorineural hearing loss and locating cochlear area.

Treatment can be performed according to the following procedures by using the device provided in the present disclosure:

Step 1, evaluating sensorineural hearing loss and locating cochlear area: conducting hearing evaluation on a patient to determine the nature and degree of hearing loss of the patient; as to an animal model, mainly conducting modeling with ototoxic hearing loss, and evaluating the degree of hearing loss thereof by hearing threshold detection; and locating and diagnosing the lesion area of the cochlea by using medical imaging diagnosis technique (for the patient) and immunohistochemical staining (for the animal model).

Step 2, selecting the ultrasonic transducer module: selecting a designated ultrasonic transducer module according to the object of intervention and the difference in the position and the cochlea, such that the ultrasonic waves emitted by the selected ultrasonic transducer module are suitable for penetrating the skin and the skull so as to act on a particular lesion area.

Step 3, performing ultrasonic treatment on the cochlea (diseased part) of the patient by the ultrasonic wave generation device for hearing recovery treatment provided in the present disclosure;

Step 4, monitoring the treatment process: monitoring the parameters of physical signs, such as electroencephalogram, electrocardiogram and blood pressure, of the patient or animal model during the treatment.

Step 5, evaluating the effect of treatment: after a course of treatment (7 days) with ultrasonic control therapy, examining the patient by clinical observation, patient complaints, hearing evaluation, medical imaging diagnosis technique, etc. to evaluate the effect of treatment; or examining the animal model by electrophysiological means, immunohistochemical staining, hearing threshold detection and auditory learning and training to evaluate the effect of treatment.

When implemented in the form of software functional units and sold or used as independent products, the functions can be stored on a computer readable storage medium. Based on such understanding, the essence of the technical solutions of the present disclosure in other words, the part of the technical solutions of the present disclosure that makes contributions to the prior art, or part of the technical solutions can be embodied in the form of a software product, and the computer software product is stored on a storage medium, comprising some instructions for enabling one computer device (which can be a personal computer, a server, a network device or the like) to execute all or some of the steps of the methods in the embodiments of the present disclosure. The aforesaid storage medium includes various mediums capable of storing program codes, such as a USB flash disk, a mobile hard disk, a read-only memory (ROM), a random access memory (RAM), a magnetic disk, or an optical disk.

The above description is only embodiments of the present disclosure, but the scope of protection of the present disclosure is not limited thereto. The changes or replacements that would readily be conceivable to those skilled in the art within the technical scope disclosed by the present disclosure shall be covered by the scope of protection of the present disclosure. Therefore, the scope of protection of the present disclosure shall be determined by the scope of protection of the appended claims.

The invention claimed is:

1. An ultrasonic wave generation device for performing a hearing recovery treatment, comprising: a wearing part and an ultrasonic wave generation part provided on the wearing part;

wherein the ultrasonic wave generation part comprises: a reference time-delay determination module, an emission sequence parameter determination module and an ultrasonic transducer module, wherein the ultrasonic transducer module comprises an activation control unit provided on the wearing part and a plurality of array elements arranged in an array, and each array element is electrically connected with the activation control unit via an independent line;

the reference time-delay determination module is configured to calculate a reference time delay of each array element when emitting an excitation pulse signal;

the emission sequence parameter determination module is configured to determine an emission sequence parameter of each array element; and the activation control unit is configured to control, according to the reference time delay and the emission sequence parameter of each array element, each array element to generate the excitation pulse signal, so that the excitation pulse signals emitted by the respective array elements are focused on a target area.

2. The ultrasonic wave generation device for performing a hearing recovery treatment according to claim 1, wherein the reference time-delay determination module comprises:

an acoustic parameter acquisition unit configured to acquire acoustic parameters of the target area, the acoustic parameters comprising density, sound velocity and attenuation coefficient; and a calculation unit configured to calculate the reference time delay of each array element according to relative position information of the target area, relative position information of the array element and the acoustic parameters which are acquired in advance.

3. The ultrasonic wave generation device for performing a hearing recovery treatment according to claim 2, wherein the acoustic parameter acquisition unit is further configured to establish a three-dimensional cochlea model according to a scan image, and calculate the acoustic parameters according to the three-dimensional cochlea model and relative position information between each array element and the target area.

4. The ultrasonic wave generation device for performing a hearing recovery treatment according to claim 1, wherein the wearing part is in shape of a flat plate and comprises a clamping part and a fixing part provided at a rear portion of the clamping part, and each array element is located on one side surface of the fixing part.

5. The ultrasonic wave generation device for performing a hearing recovery treatment according to claim 1, wherein the emission sequence parameter determination module is further configured to calculate the emission sequence parameter of each array element according to a lesion position of a cochlear, a size of the cochlea and a lesion severity of the cochlear, which are acquired in advance.

6. The ultrasonic wave generation device for performing a hearing recovery treatment according to claim 3, wherein a plurality of ultrasonic transducer modules are provided, and the ultrasonic wave generation part further comprises: an ultrasonic transducer determination module configured to determine, according to a position, a size, and a lesion severity of a lesion tissue, a corresponding ultrasonic transducer module to be used.

7. The ultrasonic wave generation device for performing a hearing recovery treatment according to claim 1, wherein the target area is cochlea.

8. The ultrasonic wave generation device for performing a hearing recovery treatment according to claim 4, wherein the clamping part has a crescent-like shape and is adapted to an outer contour of an ear.

9. The ultrasonic wave generation device for performing a hearing recovery treatment according to claim 8, wherein an elastic contact layer is provided on an inner surface of the clamping part.

10. The ultrasonic wave generation device for performing a hearing recovery treatment according to claim 3, wherein the wearing part comprises a protective housing in shape of flat plate and an adhesive layer, the plurality of array elements are all located inside the protective housing, and the adhesive layer is located on one side surface of the protective housing.

* * * * *